US011957435B2

(12) United States Patent
Ramaz et al.

(10) Patent No.: US 11,957,435 B2
(45) Date of Patent: Apr. 16, 2024

(54) ACOUSTIC-OPTICAL IMAGING METHODS AND SYSTEMS

(71) Applicants: Centre National de la Recherche Scientifique, Paris (FR); ECOLE SUPÉRIEURE DE PHYSIQUE ET DE CHIMIE INDUSTRIELLES DE LA VILLE DE PARIS, Paris (FR); SORBONNE UNIVERSITE, Paris (FR); UNIV PARIS XIII PARIS-NORD VILLETANEUSE, Villetaneuse (FR)

(72) Inventors: François Ramaz, Coulommiers (FR); Jean-Luc Gennisson, Cergy (FR); Jean-Baptiste Laudereau, Paris (FR); Clément Dupuy, Villejuif (FR); Jean-Michel Tualle, Antony (FR)

(73) Assignees: CENTRE NATIONAL DE LA RECHERCHE SCIENTIFIQUE, Paris (FR); ECOLE SUPÉRIEURE DE PHYSIQUE ET DE CHIMIE INDUSTRIELLES DE LA VILLE DE PARIS, Paris (FR); SORBONNE UNIVERSITE, Paris (FR); UNIV PARIS XIII PARIS-NORD VILLETANEUSE, Villetaneuse (FR)

( * ) Notice: Subject to any disclaimer, the term of this patent is extended or adjusted under 35 U.S.C. 154(b) by 890 days.

(21) Appl. No.: 16/979,420

(22) PCT Filed: Mar. 11, 2019

(86) PCT No.: PCT/EP2019/055990
§ 371 (c)(1),
(2) Date: Oct. 2, 2020

(87) PCT Pub. No.: WO2019/170907
PCT Pub. Date: Sep. 12, 2019

(65) Prior Publication Data
US 2021/0361169 A1    Nov. 25, 2021

(30) Foreign Application Priority Data

Mar. 9, 2018 (FR) ..................... 1852081

(51) Int. Cl.
*A61B 5/00* (2006.01)
*G01N 21/17* (2006.01)
(Continued)

(52) U.S. Cl.
CPC .......... *A61B 5/0097* (2013.01); *A61B 5/7228* (2013.01); *A61B 5/7257* (2013.01);
(Continued)

(58) Field of Classification Search
CPC ... A61B 5/0097; A61B 5/7257; A61B 5/7228; G01N 29/24; G01N 21/1702; G01N 29/2418; G02F 1/11
See application file for complete search history.

(56) References Cited

U.S. PATENT DOCUMENTS

| 4,683,750 A * | 8/1987 | Kino ...................... G01H 3/125 |
| | | 374/E11.009 |
| 2003/0030886 A1 | 2/2003 | Thomas |

(Continued)

FOREIGN PATENT DOCUMENTS

| WO | 9850781 A1 | 11/1998 |
| WO | 2016/193554 A1 | 12/2016 |
| WO | WO-2016193554 A1 * | 12/2016 ........... A61B 5/0097 |

OTHER PUBLICATIONS

International Search Report issued in PCT/EP2019/055990 dated Jun. 18, 2019 (8 pages).

(Continued)

*Primary Examiner* — John D Li
(74) *Attorney, Agent, or Firm* — HAUPTMAN HAM, LLP

(57) ABSTRACT

An acousto-optic imaging method in which light waves and unfocused acoustic waves having various directions of propagation m are emitted in a medium, by spatially modulating the amplitude of the ultrasonic transducers of an array of transducers according to several periodic spatial amplitude modulations j, and the resulting optical signal $S_{mj}(t)$ is captured. For each direction of propagation m, the signals $S_{mj}(t)$ are spatially demodulated in order to determine a signal $S_m(t)$ used to reconstruct the image of the medium.

15 Claims, 4 Drawing Sheets

(51) Int. Cl.
*G01N 29/024* (2006.01)
*G01N 29/24* (2006.01)
*G02F 1/11* (2006.01)

(52) U.S. Cl.
CPC ....... *G01N 29/024* (2013.01); *G01N 29/2418* (2013.01); *G02F 1/11* (2013.01); *G01N 21/1702* (2013.01)

(56) References Cited

U.S. PATENT DOCUMENTS

2008/0296514 A1* 12/2008 Metzger ............. G01N 21/1717
 600/407
2018/0217051 A1* 8/2018 Ramaz .................. G01N 21/49

OTHER PUBLICATIONS

Written Opinion of the International Searching Authority issued in PCT/EP2019/055990 dated Jun. 18, 2019 (11 pages).
Chiao, R.Y. et al.; "Sparse array imaging with spatially-encoded transmits"; 1997 IEEE Ultrasonics Symposium, vol. 2, Oct. 5, 1997, pp. 1679-1682 (4 pages).
Elson, D.S. et al.; "Ultrasound-mediated optical tomography: a review of current methods"; Interface Focus, Jun. 2, 2011, pp. 632-648 (17 pages).

* cited by examiner

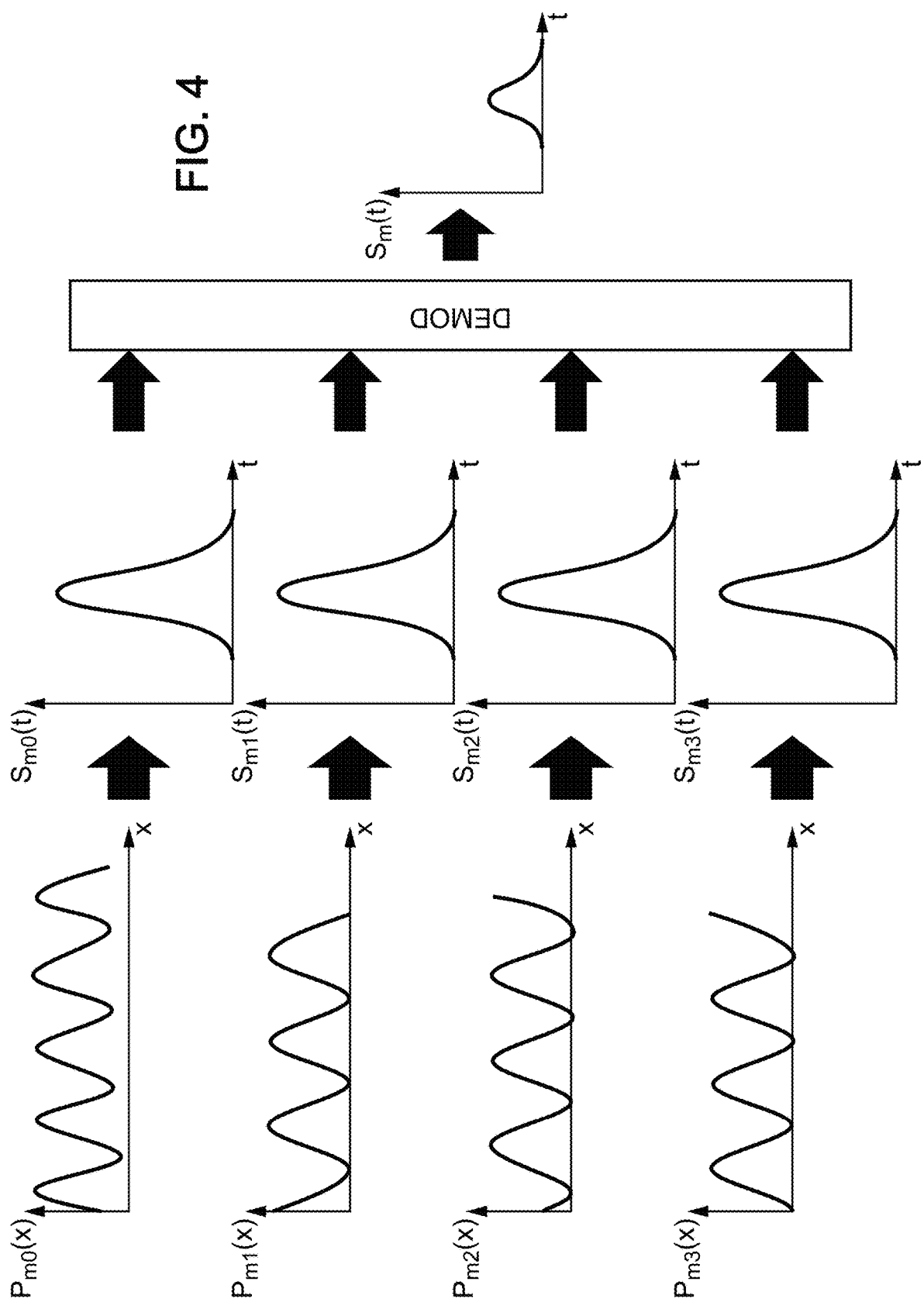

ACOUSTIC-OPTICAL IMAGING METHODS AND SYSTEMS

FIELD

The present description relates to acousto-optic imaging methods and systems.

More particularly, the invention notably relates to an acousto-optic imaging method for imaging a region of observation of a medium. Such a method is aimed at obtaining, in a non-invasive manner, information on the optical properties of a region of observation situated at a certain depth within a medium, for example biological tissues. The optical properties may for example be a color, an absorption, or else a structure of the biological tissues in the region of observation. The region of observation is for example situated at a few millimeters or centimeters depth in an object, for example inside the body, an organ or an object.

PRIOR ART

Such methods are known, in which, in the region of observation of the medium, an ultrasonic acoustic wave is generated and focused on a focal spot in the region of observation and a light wave is simultaneously emitted within this same region. By detecting a signal linked to the coupling between the light wave and the acoustic vibration in the medium information is then obtained. This is because, when an ultrasonic wave, with an acoustic frequency fa passes through a scattering medium (for example a biological or other tissue), it causes a periodic displacement of the scattering centers and a periodic modulation of the index of refraction of the medium. If an incident light wave, notably a laser light wave, of incident frequency fi is scattered by the medium, the motion of the scattering centers and the modulation of the index of refraction of the medium generate a tagged light wave comprising, on the one hand, a carrier component at the incident frequency fi and, on the other hand, an acousto-optic component scattered onto one or other of the acoustic sidebands, of frequencies fao=fa±n*fi.

Such methods are notably described in "Ultrasound-mediated optical tomography: a review of current methods" by Daniel S. Elson, Rui Li, Christopher Dunsby, Robert Eckersley and Meng-Xing Tang, published in Interface Focus (2011) vol. 1, pages 632-648.

These known methods were slow owing to the fact that they needed to scan the region of observation with a succession of focused ultrasonic waves. The formation of an image involved emitting around 200,000 focused ultrasonic waves.

Considerable progress has already been made with respect to these known methods by the invention described in the document WO2016193554, whose idea is to send into the region of observation, rather than focused ultrasonic waves, a succession of unfocused ultrasonic waves having different directions of propagation. This method allows the number of bursts of ultrasonic waves needed to form an image to be greatly limited with respect to the aforementioned conventional method. In practice, the number of bursts of ultrasonic waves may thus be divided by up to 50 in order to form an image.

SUMMARY

It turned out to be necessary to further improve the known acousto-optic imaging methods and devices, notably in order to improve their lateral resolution (namely, in a direction parallel to the array of ultrasonic transducers) without rendering the device more complex nor substantially losing in speed.

For this purpose, an acousto-optic imaging method is provided for imaging a region of observation of a medium, the method comprising a measurement step during which a plurality of measurement signals $S_{mj}(t)$ associated with unfocused acoustic waves respectively propagating in different directions of propagation m are acquired by optical means, said unfocused acoustic waves being emitted in the region of observation respectively by an array of ultrasonic transducers regularly spatially distributed, said unfocused acoustic waves being emitted, in each direction of propagation m, successively J times with J periodic spatial amplitude modulations j in order to form spatially-modulated unfocused acoustic waves, the periodic spatial amplitude modulations j having an identical spatial period in at least one direction of spatial periodicity, and corresponding to a given number P of transducers, the periodic spatial amplitude modulations j being mutually spatially phase-shifted, the measurement step comprising, for each spatial amplitude modulation j, a plurality of successive measurement operations each comprising the following sub-steps:

an acoustic emission sub-step in which an unfocused acoustic wave is emitted spatially modulated with said periodic spatial amplitude modulation j and propagating in a direction of propagation m, a light emission sub-step in which, at the same time as the spatially-modulated unfocused acoustic wave, an incident light wave is emitted in the region of observation in order to generate a spatially-modulated tagged light wave, comprising at least one acousto-optic component respectively shifted in frequency by the spatially-modulated unfocused acoustic wave, an acquisition sub-step in which the spatially-modulated tagged light wave is captured and the measurement signal $S_{mj}(t)$ is thus acquired corresponding to the periodic spatial amplitude modulation j and to the unfocused acoustic wave propagating in the direction m, a spatial demodulation step, during which the various measurement signals $S_{mj}(t)$ corresponding to the J periodic spatial amplitude modulations are combined for a same direction of propagation m, in order to obtain a demodulated signal $S_m(t)$ specific to the direction of propagation m, a processing step during which an image of at least a part of the region of observation is determined using the demodulated signals $S_m(t)$.

By virtue of these arrangements, the spatial modulation of the ultrasound waves allows, via the acousto-optic signal, information on higher spatial frequencies to be obtained and hence the lateral resolution of the image obtained to be improved.

The acousto-optic imaging method may furthermore include one and/or the other of the following features:

the array of transducers is linear and extends in said direction of spatial periodicity;

said periodic spatial amplitude modulations j are binary functions, such that only certain ultrasonic transducers are activated for a given periodic spatial amplitude modulation j; the ultrasonic transducers are thus activated according to a periodic pattern j, of period P, and the periodic spatial amplitude modulations j mutually spatially offset by a fraction of spatial period;

J is equal to 4, the spatial period corresponds to a number P of transducers being a multiple of 4 and the periodic spatial amplitude modulations are mutually spatially phase-shifted by a phase corresponding to a quarter of said spatial period;

during the spatial demodulation step, the time-domain Fourier transforms $\check{S}_{mj}(\nu)$ of the measurement signals $S_{mj}(t)$ are calculated, $\nu$ being the time-domain frequency; a signal $\check{S}_m(\nu)$ is determined by a linear combination of said time-domain Fourier transforms $\check{S}_{mj}(\nu)$; and the demodulated signal $S_m(t)$ is determined by inverse Fourier transform of the signal $\check{S}_m(\nu)$.

during the spatial demodulation step, the demodulated signal $S_m(t)$ is calculated by inverse Fourier transform of a signal $\check{S}_m(\nu)$, with:

$$\tilde{S}_m(\nu) = \tilde{S}_{0m0}(\nu) + \tilde{S}_{1m0}(\nu) + \tilde{S}_{-1m0}(\nu) \qquad (17),$$

where:

$$\tilde{S}_{0m0}(\nu) = \tfrac{1}{4}[\tilde{S}_{m0}(\nu) + \tilde{S}_{m1}(\nu) + \tilde{S}_{m2}(\nu) + \tilde{S}_{m3}(\nu)] \qquad (14)$$

$$\tilde{S}_{1m0}(\nu) = \tfrac{1}{4}[\tilde{S}_{m0}(\nu) - \tilde{S}_{m2}(\nu) - i(\tilde{S}_{m1}(\nu) - \tilde{S}_{m3}(\nu))] \qquad (15)=$$

$$\tilde{S}_{-1m0}(\nu) = \tfrac{1}{4}[\tilde{S}_{m0}(\nu) - \tilde{S}_{m2}(\nu) + \tilde{S}_{m1}(\nu) - \tilde{S}_{m3}(\nu))] \qquad (16)$$

the terms $\check{S}_{mj}(\nu)$ are the time-domain Fourier transforms of the measurement signals $S_{mj}(t)$, j is an integer in the range between 0 and 3, $\nu$ is the time-domain frequency;

the unfocused acoustic wave is chosen from between a plane acoustic wave and a divergent acoustic wave;

the directions of propagation m of the unfocused acoustic waves cover an angular sector with an angle in the range between 30 and 50 degrees;

the directions of propagation m of the unfocused acoustic waves are separated by an angular pitch in the range between 0.5 and 2 degrees;

each measurement operation is repeated L times so as to acquire L raw measurement signals $S_{mj1}(t)$ associated with each direction of propagation m of an unfocused acoustic wave and with each periodic spatial amplitude modulation j, and said L measurement signals $S_{mj1}(t)$ are averaged together in order to determine the measurement signal $S_{mj}(t)$ used for the spatial demodulation step;

each measurement signal $S_{mj}(t)$ is sampled at a frequency higher than 2 megahertz, preferably higher than ten megahertz;

the processing step comprises the implementation of an inverse Radon transformation;

the processing step comprises the implementation of a channel-formation algorithm;

the processing step comprises the implementation of a back-projection or filtered back-projection algorithm;

the processing step comprises the operations for:
determining a plurality of profile slices associated with at least one measurement signal, each profile slice being a function of a one-dimensional Fourier transform of an associated measurement signal,
determining a two-dimensional spectrum using the plurality of profile slices, and
determining at least one value representative of a light intensity in the region of observation, said representative value being a function of a two-dimensional inverse Fourier transform of the two-dimensional spectrum;

determining the two-dimensional spectrum by re-positioning in a Fourier space of the plurality of profile slices, preferably by re-positioning of each profile slice as a function of a direction of propagation of an unfocused acoustic wave associated with the measurement signal associated with the profile slice.

An acousto-optic imaging system is also provided for imaging a region of observation in a medium, the acousto-optic imaging system comprising:
an array of ultrasonic transducers spatially regularly distributed,
a light-emitting device,
a light detector,
a control device configured for acquiring, via the light detector, a plurality of measurement signals $S_{mj}(t)$ associated with spatially-modulated unfocused acoustic waves respectively propagating in different directions of propagation m, the control device being configured for:
causing said spatially-modulated unfocused acoustic waves to be emitted in the region of observation successively J times, with respectively J periodic spatial amplitude modulations j having an identical spatial period in at least one direction of spatial periodicity, and corresponding to a given number P of transducers, the periodic spatial amplitude modulations j being mutually spatially phase-shifted,
causing at least one incident light wave to be emitted by the light-emitting device in the region of observation, at the same time as each of said spatially-modulated unfocused acoustic waves, in order to generate spatially-modulated tagged light waves, each spatially-modulated tagged light wave comprising at least one acousto-optic component shifted in frequency by at least one of said spatially-modulated unfocused acoustic waves,
acquiring by the array of transducers, for each spatially-modulated tagged light wave, a measurement signal $S_{mj}(t)$ corresponding to the periodic spatial amplitude modulation j and to the unfocused acoustic wave propagating in the direction m,
carrying out a spatial demodulation by combining the J measurement signals $S_{mj}(t)$ corresponding to the various periodic spatial amplitude modulations for a same direction of propagation m, in order to obtain a demodulated signal $S_m(t)$ specific to the direction of propagation m,
determining an image of at least a part of the region of observation using the demodulated signals $S_i(t)$.

The acousto-optic imaging system may furthermore include one and/or the other of the following features:
the array of transducers is linear and extends in said direction of spatial periodicity;
said periodic spatial amplitude modulations are binary functions, such that only certain ultrasonic transducers are activated for a periodic spatial amplitude modulation j;
J is equal to 4, the spatial period corresponds to a number P of transducers being a multiple of 4 and the control device is configured for mutually spatially phase shifting said periodic spatial amplitude modulations j by a phase corresponding to a quarter of said spatial period;
the control device is configured for calculating the time-domain Fourier transforms $\check{S}(\nu)$ of the measurement signals $S_{mj}(t)$, $\nu$ being the time-domain frequency, determining a signal $\check{S}_m(\nu)$ by a linear combination of said time-domain Fourier transforms $\check{S}_{mj}(\nu)$, and determining the demodulated signal $S_m(t)$ by inverse Fourier transform of the signal $\check{S}_m(\nu)$.

the control device is configured for calculating the demodulated signal $S_m(t)$ by inverse Fourier transform of a signal $\check{S}_m(\nu)$, with:

$$\check{S}_m(\nu)=\check{S}_{0m0}(\nu)+\check{S}_{1m0}(\nu)+\check{S}_{-1m0}(\nu) \quad (17),$$

where:

$$\check{S}_{0m0}(\nu)=\tfrac{1}{4}[\check{S}_{m0}(\nu)+\check{S}_{m1}(\nu)+\check{S}_{m2}(\nu)+\check{S}_{m3}(\nu)] \quad (14)$$

$$\check{S}_{1m0}(\nu)=\tfrac{1}{4}[\check{S}_{m0}(\nu)-\check{S}_{m2}(\nu)-i(\check{S}_{m1}(\nu)-\check{S}_{m3}(\nu))] \quad (15)=$$

$$\check{S}_{-1m0}(\nu)=\tfrac{1}{4}[\check{S}_{m0}(\nu)-\check{S}_{m2}(\nu)+i(\check{S}_{m1}(\nu)-\check{S}_{m3}(\nu))] \quad (16)$$

the terms $\check{S}_{mj}(\nu)$ are the time-domain Fourier transforms of the measurement signals $S_{mj}(t)$, j is an integer in the range between 0 and 3, $\nu$ is the time-domain frequency;

the control device is configured for acquiring L raw measurement signals $S_{ij1}(t)$ associated with each direction of propagation m of an unfocused acoustic wave and with each periodic spatial amplitude modulation j, and in which said L measurement signals $S_{mj1}(t)$ are averaged together in order to determine the measurement signal $S_{mj}(t)$ used for the spatial demodulation.

BRIEF DESCRIPTION OF THE DRAWINGS

Other features and advantages of the invention will become apparent in the course of the following description of one of its embodiments, presented by way of non-limiting example, with regard to the appended drawings.

In the drawings:

FIG. 4 illustrates the spatial modulation introduced by the activation of the transducers according to a series of periodic patterns, and the later demodulation.

MORE DETAILED DESCRIPTION

In the various figures, the same references denote identical or similar elements.

Figure 1:
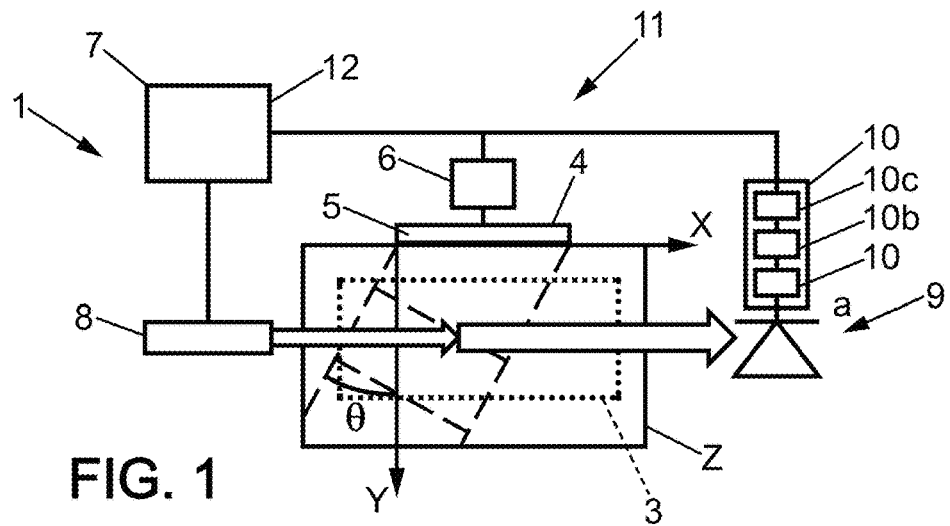
FIG. 1 is a schematic representation of one example of acousto-optic imaging system such as previously described.

FIG. 1 shows schematically an acousto-optic imaging system 1 according to one embodiment of the invention.

Thus, a medium 2, for example an object or a biological tissue, is to be imaged and hence comprises a region of observation 3. The region of observation 3 can be on the surface of the medium 2 but may potentially be located at a given depth in the medium 2, for example at a few centimeters in depth.

The medium 2 is a scattering medium. "Scattering medium" is understood notably to mean that, beyond a characteristic thickness l* (mean free path of transport), which is for example of the order of a millimeter in the biological media, the information that a light wave passing through the medium contains is totally scrambled and impossible to interpret without processing. This therefore renders a conventional optical imaging at a depth impossible. This phenomenon is also called multiple scattering of the light.

An array 4 of ultrasonic transducers is in acoustic contact with the medium 2, either directly in contact, or for example acoustically coupled to the medium 2 via a coupling element such as a vessel filled with water or a cushion filled with water.

The array 4 of ultrasonic transducers is for example a linear array comprising, for example, a few tens of transducers 5 (for example from 100 to 300). The transducers 5 are for example juxtaposed along an axis X. In variant embodiments, the transducers 5 could also be disposed following a curve, or else arranged so as to form a two-dimensional matrix. In one particular example, the array 4 of ultrasonic transducers is a linear array of 192 transducers.

The array 4 of ultrasonic transducers is controlled by control means which comprise for example an electronics rack 6 and a micro-computer 7 controlling the electronics rack 6.

The array 4 of ultrasonic transducers is thus capable of generating, in the region of observation 3, an unfocused acoustic wave propagating in a predefined direction of propagation. The direction of propagation may be controlled so as to generate, in the region of observation 3, unfocused acoustic waves propagating in various directions of propagation.

In a non-limiting manner, the array 4 of ultrasonic transducers is for example capable of generating, in the region of observation 3, an ultrasonic wave having a central frequency of the order of a few megahertz, for example 6 MHz. The array 4 of ultrasonic transducers is for example capable of generating, in the region of observation 3, a plurality of ultrasonic waves having directions of propagation chosen within an angular sector with an angle greater than 30 degrees, for example 40 degrees.

In one embodiment of the invention, the unfocused acoustic waves are plane acoustic waves. In another embodiment, the unfocused acoustic waves are divergent acoustic waves, for example spherical waves.

In practice, the unfocused acoustic waves are advantageously pulses of a given time-domain width at half-height, typically a few μsec to a few tens of μsec.

The system 1 also comprises a light-emitting device 8. The light-emitting device 8 is designed to emit at least one incident light wave in the region of observation 3. In particular, the light-emitting device 8 is designed to emit said light wave simultaneously with the emission of an ultrasonic wave by the array 4 of ultrasonic transducers. The light-emitting device 8 is for example a laser, or generally speaking, a light-emitting device allowing the spectrum of the emitted incident light wave to be controlled.

"Light wave" is understood to mean, in the wider sense, an electromagnetic radiation able to propagate in the medium 2. In particular, this may mean an electromagnetic radiation belonging to the infrared, visible or ultraviolet spectrum.

In one example, provided purely by way of non-limiting illustration, the light-emitting device 8 is an amplified single-frequency semiconductor laser with a power of 2 Watts and wavelength of 780 nanometers (which therefore corresponds to an incident frequency fi). The polarization of the incident light wave may also be controlled. In certain embodiments, the light wave may be temporally and spatially modulated or filtered prior to penetrating into the medium 2.

The system 1 further comprises a detector 9 designed to acquire measurement signals representative of the tagged light waves. The detector 9 is thus a photodetector sensitive to one or more electromagnetic wavelengths corresponding to wavelengths of the tagged light wave. Thus, for example, the detector 9 is sensitive to an acousto-optic component generated by an interaction between an incident light wave and an unfocused acoustic wave propagating in the region of observation. The detector 9 may also be sensitive to a carrier component, namely, a component of the tagged light wave at the incident frequency fi.

The detector 9 is for example a photodiode.

The system 1 may comprise elements for pre-processing or post-processing the signal 10, potentially integrated into the detector 9. The elements for post-processing the signal 10 may for example comprise a high-pass filter 10a, a wideband amplifier 10b (for example Thorlabs, DHPVA) and an analog-digital converter 10c.

Thus, in particular, the measurement signal may be sampled by the analog-digital converter 10c at a frequency greater than a few megahertz, preferably greater than ten megahertz, for example a sampling frequency of 40 MHz.

In this way, each measurement signal may notably comprise a temporal series of values of light intensity of an acousto-optic component of a tagged light wave shifted in frequency by an unfocused acoustic wave.

The array of transducers 4, the light-emitting device 8 and the detector 9 may thus form an acquisition device 11 of a system 1 according to the invention. Such an acquisition device 11 is notably designed to acquire a plurality of measurement signals associated with a plurality of unfocused acoustic waves such as will be detailed hereinafter.

A method for acousto-optic imaging of a region of observation of a medium is notably illustrated in more detail in FIG. 2 and may for example be implemented, by means of the system 1, in the following manner.

(a) Measurement Step

During a measurement step 100 (MES), a plurality of measurement signals associated with a plurality of unfocused acoustic (ultrasonic) waves may be acquired.

The acquisition step 100 comprises a plurality of measurement operations 150.

During each measurement operation 150, the following sub-steps are carried out:

(a1) Acoustic Emission

By means of the array of transducers 4, unfocused acoustic waves, for example pulses, are generated in the region of observation 3, propagating in a direction of propagation making an angle θ with the axis Y perpendicular to the direction X in the plane of the image (which is also the angle between the axis X and the equiphase straight lines in the case of plane waves). The acoustic waves are emitted in several directions of propagations, each denoted by an index m, each making an angle $\theta_m$ with the axis Y. The directions of propagation m may cover an angular sector in the range between 30 and 50 degrees, for example 40 degrees. The directions of propagation m of the unfocused acoustic waves may be separated by an angular pitch in the range between 0.5 degree and 2 degrees, for example 1 degree. In the case of an angular range of 40 degrees and of a pitch of degree, the number M of directions of propagations is therefore M=41.

In addition, for a same direction of propagation m, the acoustic wave is emitted J times each time applying a spatial amplitude modulation j to the transducers 5 of the array 4. The spatial amplitude modulations j are periodic, with a spatial period of P transducers $T_k$ in the direction X (the transducers $T_k$ being regularly distributed, this spatial period expressed as a number of transducers is equivalent to a certain distance xp). The spatial amplitude modulations j are spatially offset with respect to one another in the direction X.

The aforementioned spatial amplitude modulation corresponds to a spatial function A(k), periodic in +direction X, such that the signal $e_{mjk}(t)$ emitted by each transducer $T_k$ has an amplitude equal to $A(k) \cdot A_0$, where $A_0$ is a predefined number.

Figure 3:
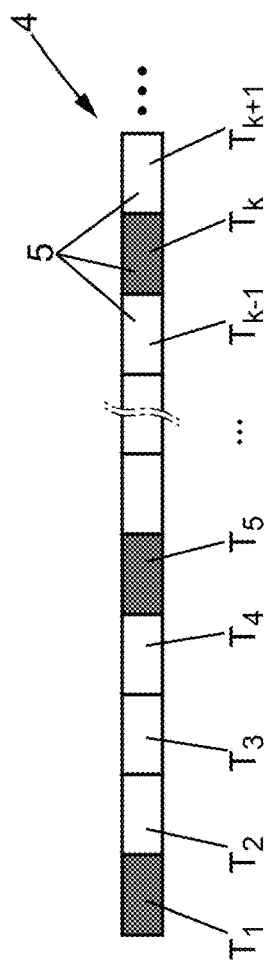
FIG. 3 shows one example of a pattern formed by the ultrasonic transducers activated in the implementation of the method in FIG. 2, in order to obtain a spatial modulation.

According to one embodiment illustrated in FIG. 3, the spatial amplitude modulation A(k) is a binary function equal to either 0 or 1 depending on the transducers $T_k$, such that only certain ultrasonic transducers are activated for a given periodic spatial modulation j.

As illustrated in FIG. 3, the transducers 5 thus activated at each emission are disposed according to a periodic pattern, having said spatial period of P transducers $T_k$ in the direction X.

The pattern formed by the transducers $T_k$ activated for each periodic spatial amplitude modulation j may take various forms. In the example in FIG. 3, only one transducer $T_k$ in 4 is activated (for an array of 192 transducers, 48 transducers for each periodic spatial amplitude modulation j are therefore activated), i.e.:

for j=0: the transducers T1, T5, etc. are activated (colored black in FIG. 3).
for j=1: the transducers T2, T6, etc. are activated.
for j=2: the transducers T3, T7, etc. are activated.
for j=3: the transducers T4, T8, etc. are activated.

As illustrated in FIG. 4, the periodic spatial amplitude modulations j lead to a periodic variation of the pressure $P_{mj}(t)$ along X generated by the ultrasonic waves, and this pressure curve is laterally shifted by P/4 along X from one periodic spatial amplitude modulation j to the other.

(a2) Light Emission

During the acoustic emission, by means of the light-emitting device 8, an incident light wave is emitted in the region of observation 3, in order to generate a tagged light wave comprising at least one acousto-optic component shifted in frequency by the unfocused acoustic wave.

(a3) Acquisition

For each direction of propagation m and periodic spatial amplitude modulation j, a measurement signal S (t) (t denoting time) representative of the tagged light wave is acquired by means of the detector 9.

In total, n=M*J signals $S_{mj}(t)$ are acquired in the measurement step 100. For M=41 and J=4, n=164 signals $S_{mj}(t)$ are therefore acquired.

In one embodiment of the invention, each measurement operation 150 is repeated L times in order to acquire L measurement signals $S_{mjl}(t)$ which are then averaged together for each value of m and j in order to obtain signals Smit) used in the following part of the processing. L may for example be greater than ten, for example a hundred times or a thousand times. For M=41, J=4 and L=1000, 164,000 bursts of acoustic waves are therefore carried out in order to obtain an image of the medium 2.

(b) Spatial Demodulation

Figure 2:
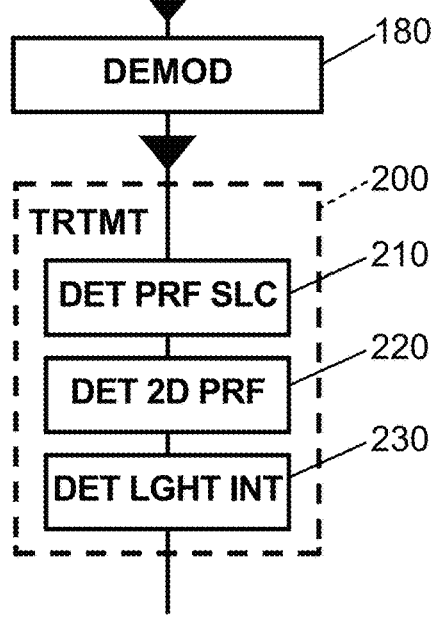
FIG. 2 is a schematic flow diagram of an acousto-optic imaging method implementing this system.

As shown in FIGS. 2 and 4, the signals $S_{mj}(t)$ are subsequently spatially demodulated in a demodulation step 180 (DEMOD). More precisely, the signals $S_{mj}(t)$ corresponding to the various periodic spatial amplitude modulations j, for a same direction of propagation m, are combined in order to obtain a signal $S_m(t)$.

In the aforementioned example, where J=4 and the spatial offset between patterns is P/4, $S_m(t)$ may be obtained by phase demodulation 4 as explained hereinafter.

Each ultrasonic wave m propagates in the medium 2. In the case of plane waves, the equiphases of this wave m are straight lines D, inclined at an angle $\theta_m$ with respect to the direction X (see FIG. 5A) which correspond to the locations of the points reached by the wave after a time t, corresponding to a distance $V_{US} \cdot t$, where $V_{US}$ is the speed of the ultrasonic wave. The excitation delay of the transducers $T_k$ (along X) is adjusted to create the inclination of the incident wave. For this purpose, each transducer $T_k$ of abscissa x has for example a delay $x \sin \theta_m / V_{US}$ with respect to a reference element.

The location of the points reached by the plane wave after a time t is therefore given by the equation:

$$x \sin \theta_m + y \cos \theta_m = V_{US} \cdot t \quad (1)$$

By way of example, the pressure generated by the ultrasonic waves emitted may be modulated along X, in a manner proportional to:

½[1+cos(2πηx+φ_j)], where:

$\eta = 1/xp$ is the spatial frequency of the spatial amplitude modulation;

$\varphi_j$ is the spatial phase of the spatial amplitude modulation j (in the case where J=4, $\varphi_j$ is equal to $j \cdot \pi/2$, j being an integer in the range between 0 and 3).

By projection, the effective spatial frequency in the direction of the wave m will be given by:

$$\eta_m = \eta / \cos \theta_m \quad (2)$$

Along the equiphases (straight lines D) there will therefore be an effective modulation of the pressure generated by the wave of the form:

$$[1+\cos(2\pi\eta_m(x \cos \theta_m - y \sin \theta_m)+\varphi_j)] \quad (3)$$

The spatio-temporal pressure may therefore be written in the following manner:

$$P_{US}(\vec{r}, t) = \frac{1}{2} f\left(t - \frac{x \sin \theta_m + y \cos \theta_m}{V_{US}}\right) \cdot \quad (4)$$
$$[1 + \cos(2\pi\eta_m(x\cos\theta_m - y\sin\theta_m) + \varphi_j)] \cdot \cos(2\pi v_{US} \cdot t)$$

where:

$v_{US}$ is the time-domain frequency of the ultrasonic waves, f(t) represents the temporal form of the ultrasonic excitation applied to each transducer 5.

The acquired signal $S_{mj}(t)$ of the tagged photons is therefore written:

$$S_{mj}(t) \propto \frac{1}{4} \int\int IN(x, y) \quad (5)$$
$$f^2\left(t - \frac{x\sin\theta_m + y\cos\theta_m}{V_{US}}\right) \cdot [1 + \cos(2\pi\eta_m(x\cos\theta_m - y\sin\theta_m) + \varphi_j)]^2 dxdy$$

where:

IN(x,y) is the signal of the image to be reconstructed (local intensity of the optical signal in the plane XY).

The time-domain Fourier transform of this signal then gives (central cross-section):

$$\tilde{S}_{mj}(v) \propto \frac{F(v)}{4} \int\int IN(x, y) \cdot \quad (6)$$
$$[1 + \cos(2\pi\eta_m(x\cos\theta_m - y\sin\theta_m) + \varphi_j)]^2 e^{-j2\pi v \frac{x\sin\theta_m + y\cos\theta_m}{V_{US}}} dxdy$$

where:

v denotes the time-domain frequency,

F(v) denotes the time-domain Fourier transform of the function $f^2(t)$.

Developing the spatial structure leads to:

$$\tilde{S}_{mj}(v) \propto \frac{F(v)}{4} \int\int IN(x, y) \left(\frac{3}{2} + 2\cos(2\pi\eta_m(x\cos\theta_m - y\sin\theta_m) + \varphi_j) + \quad (7)\right.$$
$$\left. \frac{1}{2}\cos(2\pi \cdot 2\eta_m(x\cos\theta_m - y\sin\theta_m) + 2\varphi_j) \right) e^{-i2\pi v \frac{x\sin\theta_m + y\cos\theta_m}{V_{US}}} dxdy$$

This integral is the sum of 5 terms:

$$\tilde{S}_{mj}(v) = \tilde{S}_{0mj}(v) + \tilde{S}_{1mj}(v) + \tilde{S}_{-1mj}(v) + \tilde{S}_{2mj}(v) + \tilde{S}_{-2mj}(v) \quad (8)$$

with:

$$\tilde{S}_{0mj}(v) = \frac{3F(v)}{8} \int\int IN(x, y) e^{-i2\pi v \frac{x\sin\theta_m + y\cos\theta_m}{V_{US}}} dxdy \quad (9)$$

$$\tilde{S}_{1mj}(v) = \quad (10)$$
$$e^{i\varphi_j} \frac{F(v)}{4} \int\int IN(x, y) e^{-i2\pi x\left(\frac{v\sin\theta_m}{V_{US}} + \eta_m\cos\theta_m\right)} e^{-i2\pi y\left(\frac{v\cos\theta_m}{V_{US}} - \eta_m\sin\theta_m\right)} dxdy$$

$$\tilde{S}_{-1mj}(v) = \quad (11)$$
$$e^{-i\varphi_j} \frac{F(v)}{4} \int\int IN(x, y) e^{-i2\pi x\left(\frac{v\sin\theta_m}{V_{US}} - \eta_m\cos\theta_m\right)} e^{-i2\pi y\left(\frac{v\cos\theta_m}{V_{US}} + \eta_m\sin\theta_m\right)} dxdy$$

$$\tilde{S}_{2mj}(v) = \quad (12)$$
$$e^{2i\varphi_j} \frac{F(v)}{16} \int\int IN(x, y) e^{-i2\pi x\left(\frac{v\sin\theta_m}{V_{US}} + 2\eta_m\cos\theta_m\right)} e^{-i2\pi y\left(\frac{v\cos\theta_m}{V_{US}} - 2\eta_m\sin\theta_m\right)} dxdy$$

$$\tilde{S}_{-2mj}(v) = e^{-2i\varphi_j} \frac{F(v)}{16} \quad (13)$$
$$\int\int IN(x, y) e^{-i2\pi x\left(\frac{v\sin\theta_m}{V_{US}} - 2\eta_m\cos\theta_m\right)} e^{-i2\pi y\left(\frac{v\cos\theta_m}{V_{US}} + 2\eta_m\sin\theta_m\right)} dxdy$$

Each term $\tilde{S}_{pmj}(v)$ corresponds to the projection of the signal onto a spatial frequency vector.

For each direction of propagation m, the signals for e.g. 4 values of the phase $\varphi_j$ are recorded, which correspond to spatial offsets of the pressure structure in the medium 2.

The relevant terms (p=0,1,−1) may be extracted as follows:

$$\tilde{S}_{0m0}(v) = \frac{1}{4}[\tilde{S}_{m0}(v) + \tilde{S}_{m1}(v) + \tilde{S}_{m2}(v) + \tilde{S}_{m3}(v)] \quad (14)$$

$$\tilde{S}_{1m0}(v) = \frac{1}{4}[\tilde{S}_{m0}(v) - \tilde{S}_{m2}(v) - (\tilde{S}_{m1}(v) - \tilde{S}_{m3}(v))] \quad (15)$$

$$\tilde{S}_{-1m0}(v) = \frac{1}{4}[\tilde{S}_{m0}(v) - \tilde{S}_{m2}(v) + i(\tilde{S}_{m1}(v) - \tilde{S}_{m3}(v))] \quad (16).$$

In practice, the term $\tilde{S}_{0m0}(v)$ corresponding to p=0 comprises the information obtained with non-spatially-modulated plane waves. The terms corresponding to p=1 and −1 (first-order harmonics) provide additional information in the space of the spatial frequencies and allow the quality of the reconstruction of the signal to be improved. The terms corresponding to p=2 and −2 (second-order harmonics) are preferably eliminated in order to optimize the quality of the reconstruction signal.

The three signals hereinabove are summed so as to obtain a signal $\check{S}_m(v)$ for each inclination m:

$$\check{S}_m(v) = \tilde{S}_{0m0}(v) + \tilde{S}_{1m0}(v) + \tilde{S}_{-1m0}(v) \quad (17),$$

then a demodulated signal $S_m(t)$ is deduced from this by inverse Fourier transform of $\check{S}_m(v)$.

(c) Processing

The method subsequently comprises a processing step 200 during which an image of the region of observation 3 is determined, whose pixels are representative of a light intensity in the region of observation, using the demodulated signals $S_m(t)$.

This processing step may be carried out as described in the aforementioned document WO2016193554.

Figure 5A:
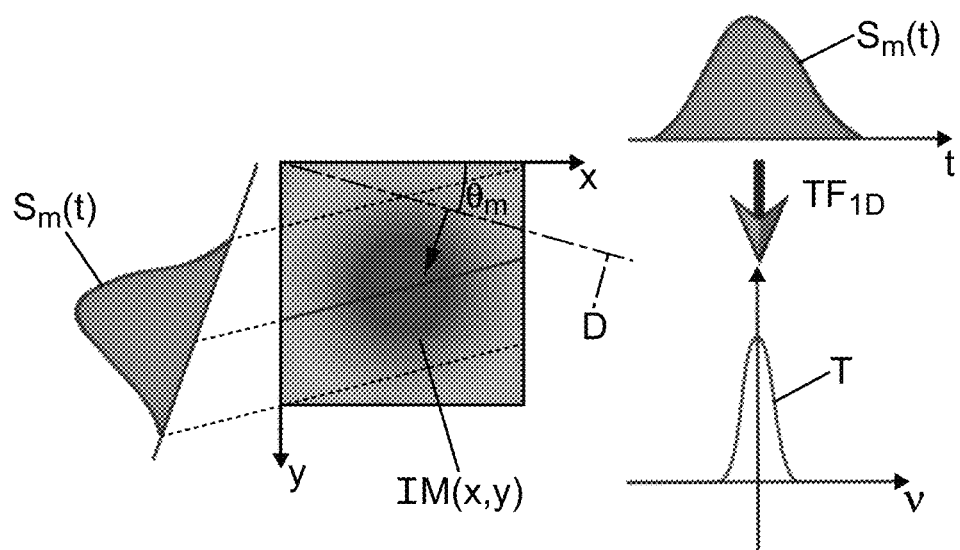
FIGS. 5A and 5B illustrate details of one embodiment of the processing step of the method in FIG. 2, FIGS. 6a-6c show images of the same medium obtained by acousto-optic imaging, respectively with focused acoustic waves, with plane waves without spatial modulation and with spatially-modulated plane waves such as previously described.
Figure 5B:
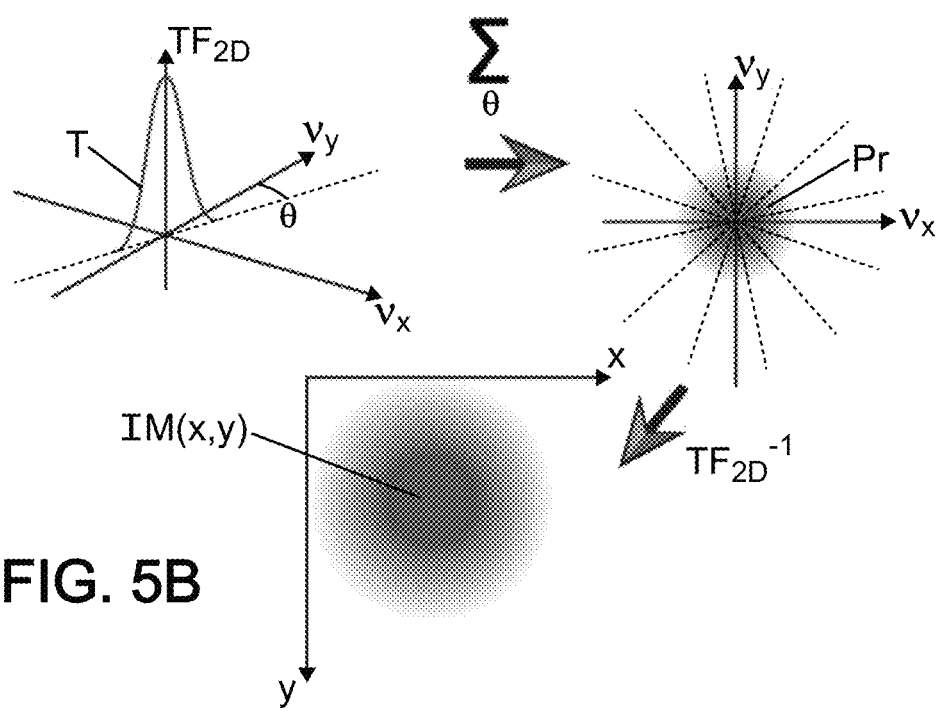

By way of non-limiting example, this processing step 200 advantageously comprises the implementation of a Radon transform as illustrated in FIGS. 5A and 5B. The processing step may also comprise a double Fourier transform (time-domain, then spatial).

Schematically, the processing step 200 (TRTMT) may comprise the following operations:

determine (210—DET PRF SLC) a plurality of profile slices associated with the plurality of demodulated signals $S_i(t)$ (FIG. 5A), determine (220—DET 2D PRF) a two-dimensional profile using the plurality of profile slices (FIG. 5B), and determine (230—DET LGHT INT) at least one value representative of a light intensity in the region of observation using the two-dimensional profile (also FIG. 5B).

More precisely, start by determining, for each demodulated signals $S_i(t)$, a profile slice T.

For this purpose, a one-dimensional Fourier transform of the demodulated signals $S_i(t)$ is implemented which supplies the associated profile slice T as illustrated in FIG. 5A.

Then, using the plurality of profile slices T associated with the plurality of demodulated signals $S_i(t)$, a two-dimensional profile P is determined. As is illustrated in FIG. 5B, the two-dimensional profile P is determined by re-positioning in a Fourier space of the plurality of profile slices. Each profile slice T is thus re-positioned in the Fourier space as a function of the direction of propagation m of the unfocused acoustic wave which was associated with the demodulated signals $S_m(t)$ associated with the profile slice T.

Thus, it is for example possible to re-position the profile slices T so as to fill the angular sector formed by the directions of propagation of the unfocused waves.

Once the two-dimensional profile P has been obtained, it is then possible to determine one or more value(s) representative of a light intensity IN(x,y) in the region of observation 3 by an inverse two-dimensional Fourier transform of the two-dimensional profile Pr, as also illustrated in FIG. 5B.

In some embodiments of the invention, the profile slices T may be completed so as to determine the two-dimensional profile Pr.

Figure 6:
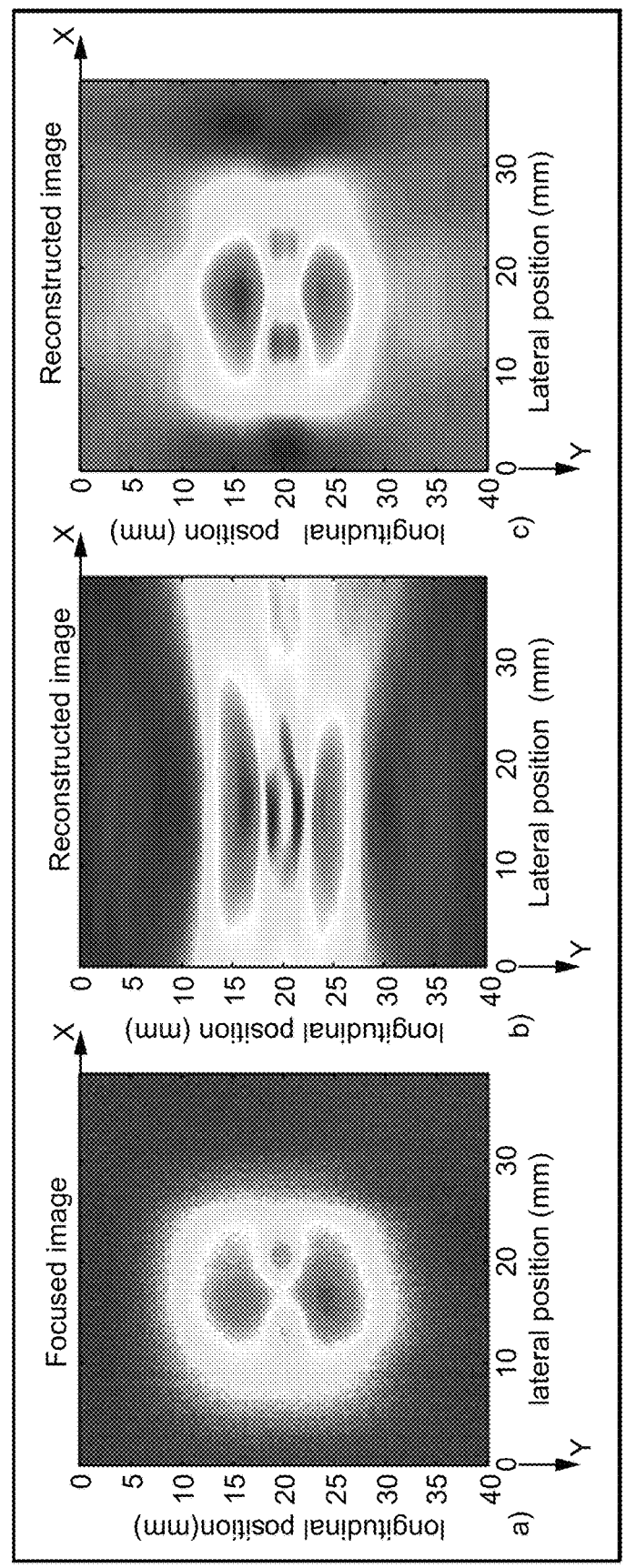

FIG. 6c illustrates an image of a medium comprising two inclusions obtained during the implementation of one exemplary embodiment of the method described hereinabove (with M=41, J=4, L=1000). FIGS. 6a and 6b are images of the same medium respectively obtained by acousto-optic imaging with focused acoustic waves and by acousto-optic imaging such as described in the aforementioned document WO2016193554.

With respect to the image in FIG. 6b the improvement in lateral resolution is clear. With respect to the image in FIG. 6a the resolution is comparable but the image in FIG. 5c can be obtained around 10 times faster than that in FIG. 6a.

The invention claimed is:

1. An acousto-optic imaging method for imaging a region of observation of a medium, the method comprising:
    a measurement step during which a plurality of measurement signals $S_{mj}(t)$ associated with unfocused acoustic waves respectively propagating in various directions of propagation m, are acquired by optical measurement, said unfocused acoustic waves being respectively emitted in the region of observation by an array of ultrasonic transducers regularly spatially distributed, said unfocused acoustic waves being emitted, in each direction of propagation m, successively J times with respectively J periodic spatial amplitude modulations j in order to form spatially-modulated unfocused acoustic waves, the periodic spatial amplitude modulations j having an identical spatial period in at least one direction of spatial periodicity, and corresponding to a given number P of ultrasonic transducers, the periodic spatial amplitude modulations j being mutually spatially phase-shifted, the measurement step comprising, for each periodic spatial amplitude modulation j, a plurality of successive measurement operations comprising the following sub-steps:
        an acoustic emission sub-step in which a spatially-modulated unfocused acoustic wave is emitted with said periodic spatial amplitude modulation j and propagates in a direction of propagation m,
        a light emission sub-step in which, at the same time as the spatially-modulated unfocused acoustic wave, an incident light wave is emitted, by a light-emitting device allowing a sprectrum of the emitted incident light wave to be controlled, in the region of observation in order to generate a spatially-modulated-tagged light wave, comprising at least one acousto-optic component respectively shifted in frequency by the spatially-modulated unfocused acoustic wave,
        an acquisition sub-step in which the spatially-modulated tagged light wave is captured by a light detector and a measurement signal $S_{mj}(t)$ is thus acquired corresponding to the periodic spatial amplitude modulation j and to the unfocused acoustic wave propagating in the direction m,
        said plurality of successive measurement operations thus acquiring the plurality of measurement signals $S_{mj}(t)$,
    for each direction of propagation m, a spatial demodulation step, during which the plurality of measurement signals $S_{mj}(t)$ corresponding to the J periodic spatial amplitude modulations are combined for the considered direction of propagation m, in order to obtain a demodulated signal $S_m(t)$ specific to the considered direction of propagation m, thus obtaining a plurality of demodulated signals $S_m(t)$, and
    a processing step during which an image of at least a part of the region of observation is determined using said plurality of demodulated signals $S_m(t)$.

2. The acousto-optic imaging method as claimed in claim 1, in which the array of transducers is linear and extends in said direction of spatial periodicity.

3. The acousto-optic imaging method as claimed in claim 1, in which said periodic spatial amplitude modulations j are binary functions, such that only certain ultrasonic transducers are activated for a given periodic spatial amplitude modulation j.

4. The acousto-optic imaging method as claimed in claim 1, in which J is equal to 4, said spatial period corresponds to a number P of transducers being a multiple of 4, and the periodic spatial amplitude modulations j are mutually spatially phase-shifted by a phase corresponding to a quarter of said spatial period.

5. The acousto-optic imaging method as claimed in claim 4, in which, during the spatial demodulation step, the demodulated signal $S_{mj}(t)$ is calculated by inverse Fourier transform of a signal $\check{S}_m(\nu)$, with:

$$\tilde{S}_m(\nu) = \tilde{S}_{0m0}(\nu) + \tilde{S}_{1m0}(\nu) + \tilde{S}_{-1m0}(\nu) \qquad (17),$$

where:

$$\tilde{S}_{0m0}(\nu) = \tfrac{1}{4}[\tilde{S}_{m0}(\nu) + \tilde{S}_{m1}(\nu) + \tilde{S}_{m2}(\nu) + \tilde{S}_{m3}(\nu)] \qquad (14)$$

$$\tilde{S}_{1m0}(\nu) = \tfrac{1}{4}[\tilde{S}_{m0}(\nu) - \tilde{S}_{m2}(\nu) - i(\tilde{S}_{m1}(\nu) - \tilde{S}_{m3}(\nu))] \qquad (15) =$$

$$\tilde{S}_{-1m0}(\nu) = \tfrac{1}{4}[\tilde{S}_{m0}(\nu) - \tilde{S}_{m2}(\nu) + i(\tilde{S}_{m1}(\nu) - \tilde{S}_{m3}(\nu))] \qquad (16)$$

the terms $\check{S}_{mj}(\nu)$ are the time-domain Fourier transforms of the measurement signals $S_{mj}(t)$,
j is an integer in the range of 0 to 3,
$\nu$ is the time-domain frequency.

6. The acousto-optic imaging method as claimed in claim 1, in which the unfocused acoustic wave is chosen from a plane acoustic wave and a divergent acoustic wave.

7. The acousto-optic imaging method as claimed in claim 1, in which the directions of propagation m of the unfocused acoustic waves cover an angular sector with an angle in the range between 30 and 50 degrees.

8. The acousto-optic imaging method as claimed in claim 1, in which the directions of propagation m of the unfocused acoustic waves are separated by an angular pitch in the range between 0.5 and 2 degrees.

9. The acousto-optic imaging method as claimed in claim 1, in which each measurement operation is repeated L times so as to acquire L raw measurement signals $S_{mjl}(t)$ associated with each direction of propagation m of an unfocused acoustic wave and with each periodic spatial amplitude modulation j, and in which said L raw measurement signals $S_{mjl}(t)$ are averaged together in order to determine the measurement signal $S_{mj}(t)$ used for the spatial demodulation step.

10. An acousto-optic imaging system for imaging a region of observation of a medium, the acousto-optic imaging system comprising:
an array of ultrasonic transducers regularly spatially distributed,
a light-emitting device allowing a sprectrum of emitted light to be controlled,
a light detector,
a control device configured for acquiring, via the light detector, a plurality of measurement signals $S_{mj}(t)$ associated with spatially-modulated unfocused acoustic waves respectively propagating in different directions of propagation m,
the control device being configured for:
causing said spatially-modulated unfocused acoustic waves to be emitted in the region of observation successively J times, with respectively J periodic spatial amplitude modulations j having an identical spatial period in at least one direction of spatial periodicity, and corresponding to a given number P of ultrasonic transducers, the periodic spatial amplitude modulations j being mutually spatially phase-shifted,
causing at least one incident light wave to be emitted by the light-emitting device in the region of observation, at the same time as each of said spatially-modulated unfocused acoustic waves, in order to generate spatially-modulated tagged light waves, each spatially-modulated tagged light wave comprising at least one acousto-optic component shifted in frequency by at least one of said spatially-modulated unfocused acoustic waves,
acquiring by the light detector, for each spatially-modulated tagged light wave, a measurement signal $S_{mj}(t)$ corresponding to the periodic spatial amplitude modulation j and to the unfocused acoustic wave propagating in the direction m, thus acquiring a plurality of measurement signals $S_{mj}(t)$,
for each direction of propagation m, carrying out a spatial demodulation by combining the plurality of measurement signals $S_{mj}(t)$ corresponding to the J periodic spatial amplitude modulations for the considered direction of propagation m, in order to obtain a demodulated signal $S_m(t)$ specific to the considered direction of propagation m, thus obtaining a plurality of demodulated signals $S_m(t)$,
determining an image of at least a part of the region of observation using said plurality of demodulated signals $S_m(t)$.

11. The acousto-optic imaging system as claimed in claim 10, in which the array of transducers is linear and extends in said direction of spatial periodicity.

12. The acousto-optic imaging system as claimed in claim 10, in which said periodic spatial amplitude modulations j are binary functions, such that only certain ultrasonic transducers are activated for a given periodic spatial amplitude modulation j.

13. The acousto-optic imaging system as claimed in claim 10, in which J is equal to 4, said spatial period corresponds to a number P of transducers being a multiple of 4 and the control device is configured for mutually spatially phase shifting said periodic spatial amplitude modulations j by a phase corresponding to a quarter of said spatial period.

14. The acousto-optic imaging system as claimed in claim 13, in which the control device is configured for calculating the demodulated signal $S_m(t)$ by inverse Fourier transform of a signal $\check{S}_m(\nu)$, with:

$$\tilde{S}_m(\nu) = \tilde{S}_{0m0}(\nu) + \tilde{S}_{1m0}(\nu) + \tilde{S}_{-1m0}(\nu) \qquad (17),$$

where:

$$\tilde{S}_{0m0}(\nu) = \tfrac{1}{4}[\tilde{S}_{m0}(\nu) + \tilde{S}_{m1}(\nu) + \tilde{S}_{m2}(\nu) + \tilde{S}_{m3}(\nu)] \qquad (14)$$

$$\tilde{S}_{1m0}(\nu) = \tfrac{1}{4}[\tilde{S}_{m0}(\nu) - \tilde{S}_{m2}(\nu) - i(\tilde{S}_{m1}(\nu) - \tilde{S}_{m3}(\nu))] \qquad (15) =$$

$$\tilde{S}_{-1m0}(\nu) = \tfrac{1}{4}[\tilde{S}_{m0}(\nu) - \tilde{S}_{m2}(\nu) + i(\tilde{S}_{m1}(\nu) - \tilde{S}_{m3}(\nu))] \qquad (16)$$

the terms $\check{S}_{mj}(\nu)$ are the time-domain Fourier transforms of the measurement signals $S_{mj}(t)$,
j is an integer in the range of 0 to 3,
$\nu$ is the time-domain frequency.

15. The acousto-optic imaging system as claimed in claim 10, in which the control device is configured for acquiring L raw measurement signals $S_{mj1}(t)$ associated with each direction of propagation m of an unfocused acoustic wave and with each periodic spatial amplitude modulation j, and in which said L measurement signals $S_{mj1}(t)$ are averaged together in order to determine the measurement signal $S_{mj}(t)$ used for the spatial demodulation.

\* \* \* \* \*